US011323196B1

(12) United States Patent
Newton et al.

(10) Patent No.: US 11,323,196 B1
(45) Date of Patent: May 3, 2022

(54) SYSTEMS AND METHODS FOR REAL-TIME TRANSMISSION OF DIGITAL DATA USING A PLURALITY OF CHANNELS

(71) Applicant: TeleTracking Technologies, Inc., Pittsburgh, PA (US)

(72) Inventors: Scott Newton, Pittsburgh, PA (US); Jason Spector, Pittsburgh, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 128 days.

(21) Appl. No.: 16/167,160

(22) Filed: Oct. 22, 2018

Related U.S. Application Data

(63) Continuation-in-part of application No. 15/958,584, filed on Apr. 20, 2018, now Pat. No. 10,937,543.

(60) Provisional application No. 62/575,142, filed on Oct. 20, 2017, provisional application No. 62/575,360, (Continued)

(51) Int. Cl.
| | |
|---|---|
| *H04J 3/16* | (2006.01) |
| *H04M 11/06* | (2006.01) |
| *H04Q 11/04* | (2006.01) |
| *H04L 67/01* | (2022.01) |
| *H04L 69/329* | (2022.01) |
| *G16H 40/20* | (2018.01) |
| *H04B 7/0417* | (2017.01) |

(52) U.S. Cl.
CPC ........... *H04J 3/1682* (2013.01); *G16H 40/20* (2018.01); *H04B 7/0417* (2013.01); *H04L 67/42* (2013.01); *H04L 69/329* (2013.01); *H04M 11/068* (2013.01); *H04Q 11/04* (2013.01)

(58) Field of Classification Search
CPC ..... H04J 3/1682; G16H 40/20; H04B 7/0417; H04L 67/42; H04L 69/329; H04M 11/068; H04Q 11/04
USPC ........................................................ 370/442
See application file for complete search history.

(56) References Cited

U.S. PATENT DOCUMENTS

| | | | | |
|---|---|---|---|---|
| 8,751,039 B1 * | 6/2014 | Macoviak | .............. | G16H 80/00 700/244 |
| 8,799,009 B2 * | 8/2014 | Mellin | .................. | G06Q 10/06 705/2 |

(Continued)

*Primary Examiner* — Pankaj Kumar
*Assistant Examiner* — Kokou R Detse
(74) *Attorney, Agent, or Firm* — Ference & Associates LLC

(57) ABSTRACT

Disclosed embodiments include systems, methods, and media for receiving and transmitting digital data over a plurality of channels. Disclosed embodiments may include receiving data from a plurality of sources through one or more networks. Disclosed embodiments may also include assigning a geographic area to the data from the plurality of sources, the geographic area corresponding to one or more locations associated with the data. Additionally, disclosed embodiments may include determining health effects for a predetermined location based on the data and its associated geographic locations. Further, disclosed embodiments may include generating, by querying a predetermined response database, instructions that address the determined health affects for the predetermined location, the instructions including an action and an associated device. And, disclosed embodiments may include transmitting, to the associated device, the action associated with the instructions.

20 Claims, 3 Drawing Sheets

Related U.S. Application Data filed on Oct. 20, 2017, provisional application No. 62/488,015, filed on Apr. 20, 2017.

(56) References Cited

U.S. PATENT DOCUMENTS

| | | | |
|---|---|---|---|
| 2011/0307284 A1* | 12/2011 | Thompson | G16H 40/40 705/7.13 |
| 2014/0088997 A1* | 3/2014 | Arefieg | G06Q 10/087 705/2 |
| 2018/0039736 A1* | 2/2018 | Williams | G16H 40/20 |

* cited by examiner

SYSTEMS AND METHODS FOR REAL-TIME TRANSMISSION OF DIGITAL DATA USING A PLURALITY OF CHANNELS

CROSS-REFERENCE TO RELATED APPLICATIONS

This application is a continuation-in-part of U.S. patent application Ser. No. 15/958,584, filed Apr. 20, 2018, which claims priority to U.S. Provisional Application No. 62/488,015, filed Apr. 20, 2017, the entirety of which are incorporated herein by reference. This application also claims priority to U.S. Provisional Application No. 62/575,142, filed on Oct. 20, 2017, and priority to U.S. Provisional Application No. 62/575,360, filed on Oct. 20, 2017, the entireties of which are incorporated by reference.

TECHNICAL FIELD

The present disclosure relates generally to the field of real-time transmission of digital data. More particularly, disclosed embodiments may be directed to receiving and transmitting digital data over a plurality of channels.

BACKGROUND

Current computing systems may be limited in the number of data sources from which they gather data. For example, certain institutional computing systems may be limited in the channels through which they can receive, process, and transmit data. In the context of business, systems may require a certain portal to enter data, which may need to be formatted in a specific manner to be used by the system. In other contexts, such as healthcare, electronic records may be limited by receiving information through a single data entry point.

SUMMARY

Disclosed embodiments include systems, methods, and media for receiving and transmitting digital data over a plurality of channels. Disclosed embodiments may include receiving data from a plurality of sources through one or more networks. Disclosed embodiments may also include assigning a geographic area to the data from the plurality of sources, the geographic area corresponding to one or more locations associated with the data. Additionally, disclosed embodiments may include determining health effects for a predetermined location based on the data and its associated geographic locations. Further, disclosed embodiments may include generating, by querying a predetermined response database, instructions that address the determined health affects for the predetermined location, the instructions including an action and an associated device. And, disclosed embodiments may include transmitting, to the associated device, the action associated with the instructions.

Consistent with other disclosed embodiments, non-transitory computer readable storage media may store program instructions, which are executed by one or more processors to perform any of the methods described herein.

The foregoing general description and the following detailed description are exemplary and explanatory only and are not restrictive of the claims.

BRIEF DESCRIPTION OF THE DRAWING

The accompanying drawing, which is incorporated in and constitutes a part of this specification, illustrates embodiments that together with the description, serve to explain the disclosed principles.

DETAILED DESCRIPTION

Figure 1:
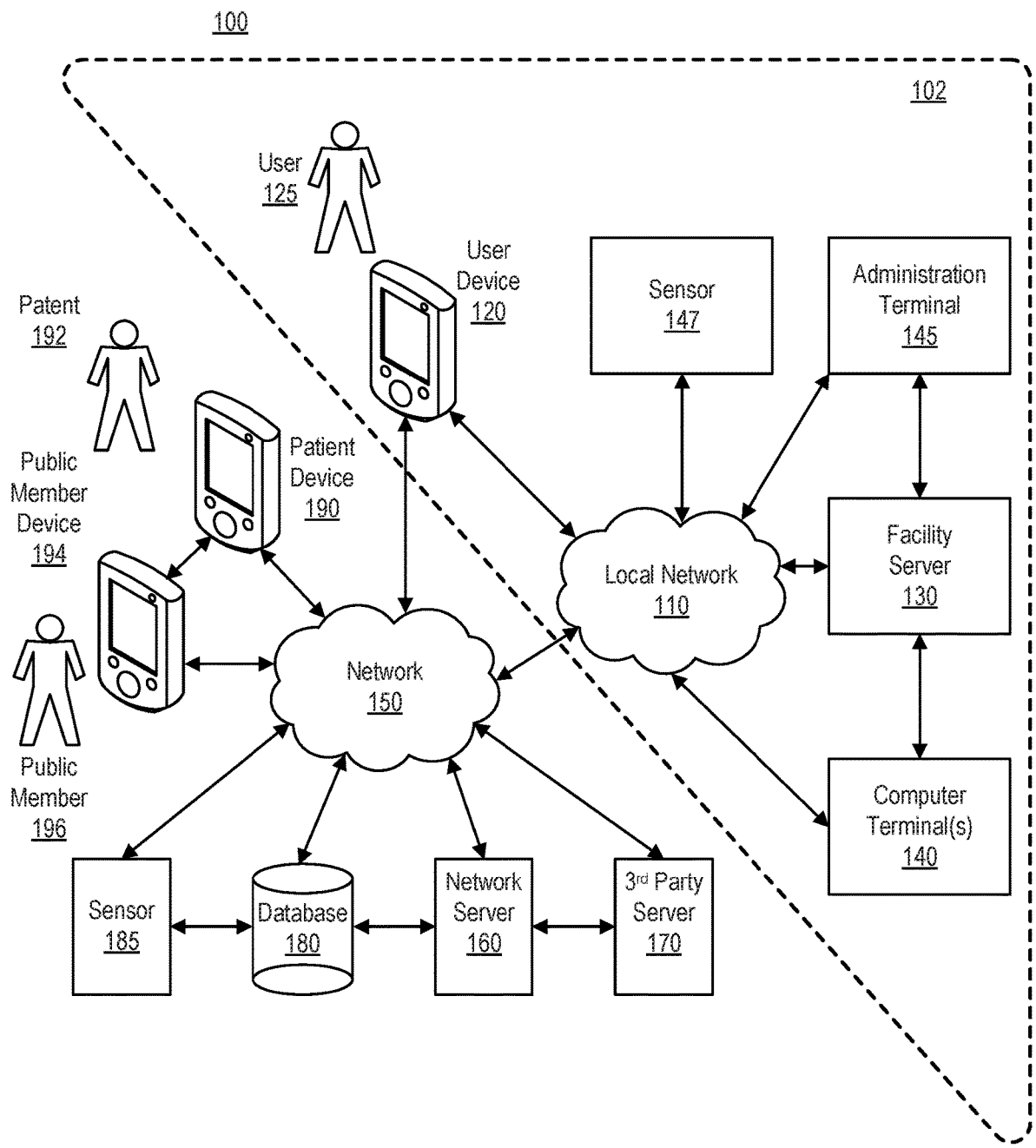
FIG. 1 depicts an exemplary computing system, consistent with embodiments of the present disclosure.

Reference will now be made in detail to exemplary embodiments, examples of which are illustrated in the accompanying drawing and disclosed herein. Wherever convenient, the same reference numbers will be used throughout the drawings to refer to the same or like parts.

Existing computing systems may be limited in the channels through which they receive and transmit data. As the number of devices capable of generating and transmitting data has increased, systems that are not able to receive, process, and analyze data from additional devices may result in such systems functioning based on inaccurate or outdated information. For example, Internet-of-Things (IoT) devices have become more widespread, providing computing platforms with additional types, quality, and amount of data to use. However, systems that are not capable of receiving and processing this data may not be able to capitalize on the additional useful information they provide.

Certain applications of computing systems may be affected by this problem in different ways. In the context of meteorological analysis, systems that are limited to the single data input of traditional wind measurement sources may result in less accurate readings than one that can receive and process pressure readings from a network of mobile phones and IoT devices. In the context of health management, a system that cannot receive and analyze IoT data from patients, their homes, and healthcare facilities may lack the capability to direct patient flow to the most appropriate and cost-effective venue of care. For example, patients experiencing non-emergency medical situations often seek medical attention by calling 911 or by visiting the Emergency Department at their local hospital. In these cases, an alternative venue often exists which may be more appropriate for their medical condition, such as an urgent care center or a secondary care clinic. However, current computing systems may lack the ability to inform and/or direct patients to alternative venues, leaving patients to believe that their only option is to seek emergency medical assistance. Additionally, emergency dispatching computing systems may lack the ability to direct every patient to the most appropriate care venue. As a result, emergency health facilities experience overcrowding and long wait times, leading to strained resources and facilities and to overwhelmed care providers. Additionally, traditional computing systems that cannot access data from multiple channels may create a system that inaccurately computes patient load, creating bloated costs for patients and for the health system.

Therefore, an improved system that intelligently gathers information from a plurality of sources over a plurality of channels, aggregating information about the patient, the health system, and the community at large may address these problems and others. Such a system may use data additional information channels to transmit control instructions through a plurality of channels. For example, the computing system may guide patients to the most appropriate care venue, control shipment of supplies to preempt needs, control community advisory delivery mechanisms (e.g., by generating targeted web advertisements), and automatically connect patients with healthcare providers. Such a computing system may be capable of coordinating healthcare operations across an entire enterprise or throughout mobile devices of population, based upon real-time patient-specific and community-wide surveillance.

Disclosed embodiments may include healthcare command centers. Healthcare command centers may vary in cost, scope and size. Such centers may reduce complexity, coordinate work efforts, enhancing communication efficiency and effectiveness by providing continuous and contextual situational awareness, while enabling proactive planning for actual and potential needs. The output of these centralized and coordinated activities may enable value through a concentration of computational resources and data, enabling disclosed embodiments to process data in more efficient ways, as well as access new types of data in combination, enabling new computations. When patients are cared for in a system that is coordinated across the care continuum, resources otherwise wasted by using multiple disparate and incompatible computing platforms can be saved. Additionally, access to care may be more timely, length of hospitalization may be reduced, direct and indirect costs of care may be reduced, and potential for preventable harm is reduced. A centralized operation may allow insight into resource utilization, giving visibility to peak-demand and under-use of extremely valuable infrastructure, resources, human capital and beds. A centralized command center may be able to assign scarce resources to emergent patient needs, while choreographing a scheduled care plan for expected patient care activities.

Caregivers are the experts at providing clinical care to patients, supporting families, and planning for courses of treatments. In existing healthcare systems, clinicians are often overtasked with burdens of providing care, operational logistics of finding and deploying supplies and equipment, while also asked to facilitate the placement of patients into the next appropriate care setting, complete with providing an excellent patient experience free from defect or harm. The overtasking of clinicians leads to cognitive overload, which is known to be a significant factor in reduced function and contributing factor to safety events. The centralized command center of certain embodiments may allow healthcare providers to offload operational aspects of providing care to a central a central computing system operated by a group of staff who develop the expertise in healthcare operations to support caregivers. Such a centralized computing system may monitor and forecast needs and deploy resources in a coordinated method to meet the needs with efficiency.

Existing healthcare environments are overwhelming caregivers and staff with continuous streams of information, and identifying priority messages is a growing challenge. According to the present disclosure, through the use of predictive analytics, message prioritization may be automated, and identified messages may be presented to caregivers and staff in simple, elegant notifications. The notifications may enable caregivers and staff to quickly identify the highest value work first, for completion within the constellation of activities performed each shift. Completion of high-value work first has a network effect that frees up beds, accelerates timeliness of treatments, and reduces the queuing effect of non-prioritized batched activities. Streamlining message prioritization and transmission may also reduce communication network loads by reducing redundant and unnecessary communications.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

FIG. 1 shows a diagram of a command system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, system 100 may include a facility server 130, a computer terminal 140, an administration terminal 145, a user device 120, network server 160, third party server 170, and database 180. The components of system 100 may communicate directly, through network 150, through local network 110, or through a combination of communications methods. In some embodiments, local network 110, facility server 130, computer terminal 140, administrator terminal 145, and user device 120 may be physically disposed within a facility such as a medical facility such as a hospital or office building (i.e. as facility system 102) while network 150, network server 160, third party server 170, and database 180 may be external to the medical facility. Other components known to one of ordinary skill in the art may be included in system 100 to perform tasks consistent with the disclosed embodiments. For example, in some embodiments, facility system 102 may include one or more sensor devices such as sensors 147 located throughout the facility to monitor one or more conditions such as occupancy, temperature, humidity, proximity, and other parameters indicative of a status or condition of a room, area, equipment, or supplies. In some embodiments, sensors 147 may be disposed throughout one or more areas of a hospital as part of a security system or a real-time locating system. Additionally, in some embodiments sensors 147 may include one or more wireless receivers (not shown) configured to detect one or more wireless sensor or locating tags, to track a location of a tagged item and/or person, or a condition about the tagged item and/or person.

Computer terminal 140 may be a standalone device disposed in an office, a room, an employee station, or an alternative central location in a workplace. In some embodiments, computer terminal 140 may be a desktop or notebook computer, a flat panel or projected display, touch screen monitor, or any other display. In some embodiments, computer terminal 140 may be associated with a particular room in a facility, such as a particular patient room, hotel room, conference room, or any other type of room. Thus, a message or task request received from a computer terminal 140 may automatically associate the task request or message with the room in which computer terminal 140 is installed.

Administrator terminal 145 may include a computer system or device associated with a user 125 that manages or oversees a portion of facility system 102. For example, administrator terminal 145 may comprise a computer system located at a head nurse station, a housekeeping manager's office, or any other department manager's office or station. In some embodiments, administrator terminal 145 may be a computer terminal 145 designated to a particular user or class of users, and may include any of the functions and comprise any of the hardware discussed with respect to computer terminal 145.

User 125 may be an employee in a workplace environment such as a physician, nurse, a technician, supervisor, manager, support personnel, dispatcher, or any other individual involved with the care of a patient. User 125 may operate computer terminal 140, user device 120, and/or another computer (not shown) to interact with system 100. System 100 may include multiple types of users such as, for example, caregivers, technicians, task requestors, dispatchers, and responders. Task requestors may include one or more individuals who initiate a request for a certain task to be completed, such as a nurse requesting a hospital bed. In some embodiments, dispatchers may include individuals who perform one or more tasks related to assigning requested tasks. In some embodiments, responders may include one or more individuals assigned to the requested tasks, who perform and complete the tasks.

User device 120 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, user device 120 may be a computer system or mobile computer device that is operated by user 125. In some embodiments, user device 120 may be associated with a particular individual such as user 125, such that task assignments directed toward user 125 are sent to mobile device 120.

In some embodiments, user device 120 may communicate with facility server 130 and/or network server 160 via direct wireless communication links (not shown), or via a combination of one or more of local network 110 and/or network 150.

In some embodiments, one or more individuals such as the patient 192 or a member of the public 196 may send and receive information to system 100. In the example shown, patient 192 may operate patient device 190, which may be similar in form and function to user device 120. In some embodiments, patient 192 may provide information regarding location, symptoms, consumer purchases, ratings for satisfaction of care, indication of delay, and any other information relevant to a patient diagnosis, or treatment protocol and itinerary.

Public member 196 may an individual associated with the patient who is not a hospital employee such as, for example, a primary care physician of the patient, or a relative of the patient. Public member 196 may operate public member device 194, which may be similar in form and function to devices 190 and 120.

Facility server 130 may be operated by a facility such as a hospital, business, retail location, and the like. Facility server 130 may enable communication within a computer-based system including computer system components such as desktop computers, workstations, tablets, hand held computing devices, memory devices, and/or internal network(s) connecting the components.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local network 110 may comprise any type of computer networking arrangement used to exchange data in a localized area, such as WiFi, Bluetooth™ Ethernet, and other suitable short-range connections that enable computer terminal 140 and user device 120 to send and receive information between the components of system 100. In some embodiments, local network 110 may be excluded, and computer terminal 140 and user device 120 may communicate with system 100 components via network 150. In some embodiments, computer terminal 140 and/or user device 120 may communicate with one or more system 100 components via a direct wired or wireless connection. In some embodiments, local network 110 may comprise a portion of network 150 or an extension of network 150.

Network server 160, third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with one or more third-party services such as mapping services, data analysis services, recommendation engines, decision support systems, or storage services. Third party server 170 may provide an application programming interface (API) that disclosed embodiments employ to interact with third party services, such as submitting queries, requesting information, and/or transmitting data. In some embodiments, third party server 170 may be associated with a system for gathering information related to consumer purchases. Additionally or alternatively, third party server 170 may be associated with a system for gathering and analyzing syndromic information throughout a community. An example of such a system may be an RODS (real-time outbreak and disease surveillance) laboratory.

According to some embodiments, a healthcare command center may be implemented in a healthcare venue such as a hospital. A healthcare command center may also be implemented in a healthcare system encompassing a number of healthcare venues; the healthcare command center may serve as the command center for some or all of the healthcare venues within the healthcare system. A healthcare command center may provide a number of services to the healthcare venue or system. Some of the services may be executed by one or more processors. In some embodiments, services may be selected according to the needs and capacity of a healthcare venue or system. In other examples, a healthcare command center may provide all available services and tools to a healthcare venue or system. Services and tools may span a continuum of care from community health to preventative health to acute care to post-acute care to reintegration of patients back into the community.

Processors within the healthcare command center may collect and analyze data to provide situational awareness indicators. For example, one or more processors may collect data pertaining to indicators of flow of patients through a healthcare venue, system, or systems. Data may be collected from one or more sensors, aggregated from electronic medical records received from networked databases, received from input on one or more computers within system 100 or in communication with system 100. Data collection and analysis may provide predictive and cognitive analytics about future trends and events within a healthcare venue, system, or systems. A healthcare command center may use collected data to plan future events or to offer recommendations to staff or caregivers about future best practices. A healthcare command center may additionally collect contextual data in real-time. For example, a healthcare command center may collect data about current demands and availabilities across a healthcare system during a period of time. This data may be used to plan or suggest future actions using predictive and statistical analyses.

In some embodiments, a healthcare command center may collect and analyze data pertaining to a developing health condition within a community. For example, a healthcare command center may collect and analyze data pertaining to a public health emergency, a population-based illness, endemic, or epidemic, an injury pattern, or any other type of clustered health condition within a community. Examples population-based illness may include, and are not limited to, flu, MERS-CoV, Ebola, and SARS. According to one example, a healthcare command center may collect and analyze data pertaining to a developing flu epidemic within a community. The healthcare command center processor(s) may analyze the data to recognize a variety of indicators in the community and predict the developing epidemic and before sick patients arrive at healthcare facilities. For example, the healthcare command center may monitor the number of purchases of flu medicine by collecting data concerning scanned consumer product codes for flu medicine. The healthcare command center may collect this and other data from the community to determine when the flu epidemic will cause patients to seek medical attention, such as at a hospital or a clinic. The collected data may be used to assess a healthcare system's current state of affairs, such as occupancy levels, projected volumes over coming days, planned procedures, outpatient and inpatient visits, etc. This data may be used to make or suggest changes such as operational changes, supply chain changes, patient intake and discharge changes, and staffing changes, to better prepare for the predicted influx of patients with the flu. These changes may be based upon, for example, historical trends.

In some embodiments, network 150 may additionally comprise one or more sensor devices 185, such as sensors located in a patient's home. Sensors 185 may include microphones and/or cameras to perform telemonitoring of a patient in a non-clinical setting, such as in the patient's home, in a vehicle associated with the patient, in an electronic device such as a smartphone or wearable associated with the patient, or in a workplace associated with the patient. Sensors 185 may include, for example, accelerometers, motion detectors, position monitors, and/or kinesis monitors.

In some embodiments, one or more of sensors 185 may be fixed to a given location. One or more of sensors 185 may be located at a portal of entry of a building (e.g., home, office, store) and/or transport (e.g., car, bus, train, plane, boat), such as a door which individuals must pass through to enter buildings and/or transports. In certain embodiments, one or more of sensors 185 may be located at highly trafficked areas within those example locations. For example, within a home, one or more of sensors 185 may be located in the kitchen, bathroom, stairway, and/or halls. The presence of a user at one of these locations may be interpreted by system 100 as an indication of mobility. For example, if a sensor detects a person traversing the stairs, system 100 may record that person as being mobile. In some embodiments, system 100 may interface with preexisting sensors at a building and/or transport. For example, system 100 may interface with a security and/or surveillance system at a building, which may enable system 100 to monitor movements within, into, and out of a building. In the context of a transport, example preexisting sensors may include dash cameras and/or GPS systems. In these examples, sensors 185 may include one or more sensors of these preexisting sensor systems.

In some embodiments, sensors 185 may include sensors of IoT devices. "Smart" appliances and other IoT devices may provide sensor data to system 100. For example, sensors 185 may include sensors from a smart refrigerator, such as sending a signal when the refrigerator door is open or shut. In another example, a smart thermostat may measure a temperature inside a building or room. In still further examples, temperature monitoring sensors may detect the heat signature of an individual within a room. Other IoT devices that may include example sensors include smart pill bottles and body weight scales. For example, a smart pill bottle may provide data to system 100 including when a bottle is open, when it is closed, and how many pills are currently in the bottle. Additional IoT devices may be used that measure personal health data, environmental factors, and/or individual activity, consistent with disclosed embodiments.

In some embodiments, one or more of sensors 185 may be wearable. Additionally, in some embodiments sensors 185 may include one or more wireless receivers (not shown) configured to detect one or more wireless sensor or locating tags, to track a location of a tagged item and/or person, or a condition about the tagged item and/or person. In some embodiments, sensors 185 may include personal physiological monitoring, such as a heart rate monitor, smart watch, and/or blood sugar monitor. Further, in some embodiments, sensors 185 may measure data from throughout a community, such as about weather conditions, temperature, air quality, ultraviolet (UV) light, and population movements.

In some embodiments, system 100 may include configurations that vary from the example shown in FIG. 1, which illustrates a facility system 102 working in concert with a cloud computing system including network server 160, third party server 170, and database 180. As a first exemplary variation, system 100 may include only facility system 102, and thus may exclude cloud computing components such as network server 160, third party server 170, and database 180. In such embodiments, facility system 102 may handle substantially all operations and functions of the present embodiments. As a second variation, system 100 may exclude components of facility system 102 such as facility server 130. In such embodiments, a cloud computing system including network server 160, third party server 170, and/or database 180 may handle some or all computing and interface-related functions of the disclosed embodiments.

In some embodiments, system 100 may include two or more facility systems 102. Each facility system 102 may include local network 110, facility server 130, computer terminal 140, administration terminal 145, sensor 147, and/or user device 120. Each facility system 102 may work in concert with a cloud computing system including network server 160, third party server 170, and database 180. In this way, system 100 may perform surveillance across a number of care facilities within a community to collect real-time data collected from a plurality of sources, and may coordinate healthcare operations in those facilities, such as transporting resources and coordinating patient flow there between. In some embodiments, system 100 may utilize information collected within a first facility 102, such as from sensor 147, in conjunction with predictive analytics to predict future health trends or patient influx in a second facility 102.

System 100 may receive information from a variety of sources, such as from sensors 147 and 185, third party server 170, and devices 120, 190, 192. System 100 may utilize that information to determine health needs of facilities 102 and throughout a community, and may additionally anticipate developing health conditions within the community and the associated patient influx into facilities 102, based upon the information and historical trend data. In some embodiments, system 100 may additionally coordinate health services within facilities 102 and/or the community. For example, data may be received from community sensors, such as sensor data from handwashing (e.g., water usage or soap dispenser usage) and door entry to shared restrooms in an apartment, store, and/or office. Increased bathroom usage may flag a potential outbreak of a gastro-intestinal virus, while comparing entrances to the bathroom with the number of times a soap dispenser is used may allow system 100 to determine that people are not washing hands, which may aid in spreading a virus or bacteria. Either or both of these data points (e.g., bathroom usage volume and soap/sink usage) may prompt system 100 to distribute a public service announcement to remind individuals to wash their hands when visiting the restroom For example, system 100 may automatically publish a message on a social media platform in response to determining that the soap and sink usage does not match the number of individuals entering restrooms at one or more facilities within a community. Using these types of sensors may also provide the technological advantage of maintaining anonymity and privacy for individuals because no personal identifying information is gathered from these types of community sensors. As another example of community sensors, system 100 may receive data from barcode scanners at convenience stores in a community. These types of sensors may identify buying trends, and based on the purchase trends, system 100 may be able to identify symptom trends. For example, system 100 may receive data regarding purchase and determine an increase in the sale of certain over-the-counter medicine. In response, system 100 may identify the symptoms those medicines treat (e.g., headache, gastro-intestinal distress, fever, sore throat) and identify potential diagnoses for the particular set of symptoms at issue. System 100 may alert at-risk patients or transmit an advisory to health providers based on these symptoms and/or their potential causes. For example, system 100 may initiate automated calls to elderly individuals in the community to provide information and connect them to a health professional to preempt or facilitate treatment of an illness in the community. Services and tools of system 100 may span a continuum of care from community health to preventative health to acute care to post-acute care to reintegration of patients back into the community.

The following are descriptions of command center embodiments according to the present disclosure. The embodiments are not exclusive, and features of the embodiments may be included within other embodiments.

Centralized Patient Placement

In some embodiments, a command center may include develop of patient-flow management expertise in the healthcare command center workforce based on critical thinking, problem solving, teamwork and high-reliability. Such expertise may be achieved with executive sponsorship and engagement. For example, one or more of a vice president, director, manager, data analyst, and administrative support personnel may be engaged. These personnel may be engaged for a predetermined length of time; for example, between six months and one year. Patient-flow management expertise may additionally be developed by engaging front line staff, such as critical care registered nurses or a hybrid model. Patient-flow management expertise may additionally be developed by issuing and following advisories pertaining to interviewing and hiring, as well as advisories pertaining to defining of job descriptions.

Some embodiments may additionally include development of closed loop communications to end users and/or clinicians to cognitively off-load tasks related to patient movements. Some embodiments may additionally include the development and delivery of "just-in-time notifications". Through the use of analytics and applied best practices, priority messages may be identified and presented to caregivers and staff in simple, elegant notifications. The notifications may enable caregivers and staff to quickly identify the highest value work first, for completion within the constellation of activities performed each shift, thus minimizing fatigue associated with or caused by a large and overwhelming number of alarms, information, and tasks. Some embodiments may additionally include burning platform advisories.

Some embodiments may include use of, or be performed with, various computer-executed tools. For example, some embodiments may utilize patient capacity management tools, such as patient admission tracking programs, patient bed tracking programs, patient transportation tracking programs, and patient tracking portals. Some embodiments may additionally include use of tools for tracking and reporting the performance of command center staff and/or health center staff. Some embodiments may additionally include real-time locating systems (RTLS), such as auto-discharge tools.

A variety of services may also be implemented during the development and delivery of a healthcare command center. These services may include, for example, workflow redesign and automation advisories; reevaluation and advisories concerning workflow policies and procedures; integration of the healthcare command center into the healthcare center and the overarching health system; call recording systems with immediate playback and integration; phone systems with multiline conference call capability; and analytics, scorecard, and interpretation advisories, wherein baseline is established prior to go-live of automation. Services may additionally include discharge process advisories; executive and operational governance advisories; development and integration of clinical protocols, standard operating procedures, and scripts; educational practices for onboarding of staff, with annual reviews for all key stakeholders with competencies; transportation networks, both medical & non-medical; ergonomics design and selection advisories; workspace design/selection advisories; executive capacity management council advisories; and organization chart advisories.

Patient Transfer Center

Some embodiments may include design, implementation, and optimization of patient access screening and triage to available options (i.e., access as a service, not destination; right patient, right venue, right price, right now). Screening and triage may be achieved by, for example, incorporation of emergent or scheduled transfer of patients for tertiary, quaternary, and/or specialty care. Some embodiments may additionally include phone consults before a patient may be transferred, allowing expert advice to be shared between clinicians. Some embodiments may include telemedicine, such as in community hospitals, post-acute settings, skilled nursing facilities, staff homes, and other remote work sites. Some embodiments may include just-in-time ambulatory clinics or clinician office visits, as well as mobile integrated health, community-based nursing staff, and paramedic visits to home and/or work.

Some embodiments may additionally include incorporation of code teams, rapid response units, and specialty-intervention teams. Examples of such teams may include trauma care teams, stroke teams, STEMI (ST-elevation myocardial infarction) teams, and sepsis teams. Some embodiments may include communication and coordination techniques with such teams.

Some embodiments may include use of, or be performed with, various computer-executed tools. For example, some embodiments may include use of tools for access management such as patient transfer control tools, community access tools, and on-call scheduling tools. Some embodiments may additionally include predictive insight tools.

A variety of services may also be included within some embodiments of a command center. These services may include, for example, incorporation of transportation networks, both medical and non-medical; ergonomics design and selection advisories; workspace design and selection advisories; referral network advisories; internal and external marketing advisories; and menu of services advisories, for internal and external clients.

Hospital Command Center

Some embodiments may include the design and installation of a model work environment to the health care center. This environment may include ergonomics, environmental controls, lighting, sound management, communications devices, utility services redundancy, and modular configurations. The environment may be capable of growth and may be scalable.

Some embodiments may additionally provide real-time data streams on current performance, resource availability, utilization, response-times, congestion and barriers, such as patient traffic monitoring and management. Additionally, some embodiments may provide development and application of care-progression, core-measure, and/or quality indicator measure monitoring, as well as itinerary-based choreographed patient care and real-time intervention for outliers or atypical patients. The provision of such data drives clinicians to highest value work first.

Integrated services may also be included within some embodiments, such as telemedicine, remote monitoring, asset tracking, automated supply chain, and partner and vendor-performance services. Some embodiments may also provide practice-based evidence to drive research into patient outcomes across the continuum of care.

In some embodiments, the command center may include provision of clinical workflow tools, as well as real-estate sourcing and selection advisory services, post-acute network advisory and automation services, and ambulatory network advisory and automation services.

Enterprise Healthcare Command Center

Some embodiments may include development and application of a unified communications and coordination center for patient access into, through and across health system based on standardized and automated workflows. It may utilize predictive analytics to anticipate needs based on forecasted patient activities, occupancy, demands, and length-of-stay data. This may include, for example, patient or resource capacity watches and warnings to prepare and/or take action. Some embodiments may additionally utilize conditional analytics to provide decision support on next-best choices when a primary option is not available. These choices may depend on, for example, clinical, financial, and/or operational indicators. Some embodiments may additionally include hospital network advisory services.

Regional Healthcare Fusion Center

Some embodiments may provide a population-health monitoring hub, wherein data pertaining to one or more the following is collected and analyzed: consumer-based purchases, homes, mass-gatherings, symptoms, environmental factors, seasonal factors, migratory patterns, and population disease-specific factors.

Some embodiments may additionally provide simulation-capable modeling for testing care-delivery methods, for guiding strategy, and for aiding in regional business-case planning to drive outcomes. A cloud-based emergency management hub may be implemented for the health system and may be integrated with public safety communications and incident commands. Some embodiments may additionally provide emergency and disaster preparedness advisory services, population health advisory services, telehealth advisory services, and market survey advisory services.

According to the present disclosure, healthcare command center delivery is intended to solve the problem of fragmented healthcare structure, complex and ad hoc process, leading to intentional and purposeful outcomes. Achievement of these outcomes occurs through a delivery method that may enable the creation of a healthcare command center that centralizes operations, standardizes and automates workflow, and consistently aggregates and reliably disseminates valuable information to system stakeholders.

Healthcare command center delivery may include bundled projects and non-bundled projects. According to some embodiments, one bundled option may include a potential to sell a full healthcare command center with all the supporting technology and services to support a hospital or healthcare system. According to some embodiments, non-bundle projects may centralize existing tools and workflow into a formal structure. Specialty expertise may be provided by, for example, internal subject matter experts with centralized healthcare command center design and deployment experience.

Service staff may provide project management, technical discovery and design, plan project resources, and manage team to implementation. Integration staff may assess and plan for standard and novel integration points with the goal of high-integration into a final healthcare command center.

Advisory services may assess a current level of organizational maturity, establish executive steering group, and create a high-level roadmap to achieve a next level of maturity using strengths and resources of the healthcare command center. They may additionally lead or enable change and transition methods for a client organization. Client success staff may manage on-going relationship across an organization to enable initial and long-term adoption coordinated with Advisory Services.

Healthcare command center SMEs may collaborate across the project from initial envisioning through post-implementation. They may provide direction on model design, best practice, staff selection, training and workflows through an iterative process with all stakeholders.

In some embodiments, a healthcare command center may be implemented according to the following exemplary method. According to some examples, the healthcare command center may be optimized periodically, based on initial impact outcomes within a first year of implementation; optimization processes and outcomes progress may be delivered within two years; and three years may allow driving to high-level outcomes while moving into a sustainment and leadership continuity phase. According to some examples, as years additional years approach (such as years four and five), redesign may be considered based on a current needs assessment and as client priorities evolve, maintaining relevance and engagement in the healthcare command center central role.

Some embodiments of a healthcare command center may include a single hospital with centralized capacity management with access management for a referral network. According to some embodiments, the healthcare command center may include patient access management tools, capacity management tools, performance reporting tools, and some limited services. According to other embodiments, the healthcare command center may include patient access management tools, capacity management tools, performance reporting products RTLS with auto-discharge tools, predicting insight tools, and comprehensive services.

Other embodiments of a healthcare command center may include single hospital management with associated referral and post-acute networks. According to some embodiments, the center may include patient access management tools, capacity management tools, performance reporting tools, and comprehensive services. According to other embodiments, the healthcare command center may include patient access management tools, capacity management tools, clinical workflow tools, performance reporting tools, RTLS with auto-discharge services, predictive insight services, comprehensive services, telemedicine, and asset tracking.

Other embodiments of a healthcare command center may include multi-hospital capacity management with referral and post-acute networks. According to some embodiments, the center may include patient access management tools, capacity management tools, predictive insight services, comprehensive services, RTLS with auto-discharge services, and asset tracking. According to other embodiments, the healthcare command center may include patient access management tools, capacity management tools, clinical workflow tools, performance reporting tools, RTLS with auto-discharge services, predictive insight services, comprehensive services, telemedicine, asset tracking, augmented and/or virtual-reality command centers.

Other embodiments of a healthcare command center may include multi-hospital and ambulatory capacity management with referral and post-acute networks, plus active public health and public safety integration. According to some embodiments, the center may include patient access management tools, capacity management tools, predictive insight services, comprehensive services, RTLS with auto-discharge services, asset tracking, post-acute integration, ambulatory and/or clinic integration. According to other embodiments, the healthcare command center may include access management tools, capacity management tools, a clinical workflow suite, performance reporting tools, RTLS with auto-discharge services, predictive insight tools, comprehensive services, telemedicine, asset tracking services, virtual-reality command centers, and community based care networks.

In some embodiments, a healthcare command center may be integrated with emergency medical services (EMS) to gain visibility into community needs. This integration may include routine medical transportation services such as ambulances and wheelchair vans, as well as integration with non-medical transportation services, such as Uber, Lyft, and taxis or other similar ride-share programs. Integration with EMS may occur at both the front-end (transportation of patients to a healthcare venue for treatment) and the back-end (transportation to post-care facilities after patient discharge), and may provide data to predict future transportation demands.

In some embodiments, front-end EMS may be integrated with the healthcare command center to provide real-time data about current demands for service and about capacities of different healthcare venues across a healthcare system. Instead of EMS services transporting all patients to an acute-care setting such as an emergency department, exemplary healthcare command centers may coordinate delivery of patients to the appropriate healthcare venue via EMS. For example, patients experiencing emergency medical situations such as stroke or heart attack may be transported to an acute-care center via EMS services such as an ambulance, while other patients experiencing less severe symptoms may be transported to an alternative venue such as an urgent care clinic via ambulance or alternatively via a different mode of transportation such as Uber or taxi. As a result, patients are transported to the appropriate venue of care, and individual venues are not overwhelmed with patients better suited for other venues.

By collecting data pertaining to transportation of patients to the correct venue care, exemplary healthcare command centers may better understand needs across a region. Collected data may better indicate needs for different venues of care such as hospitals and urgent care centers. This data may be used to plan development of specific venues within the region to better suit the demand, and may additionally be used to develop and implement telemedicine services. Collected data may additionally cause individual venues to be less overwhelmed with patients better suited for other venues. Collected data may additionally be used to predict future demands across the region, allowing planning of future venues and allocation of resources across the system that may not necessarily be aligned presently.

In some embodiments, healthcare command centers may additionally be integrated with back-end care systems that manage discharge of patients. Data collected by the healthcare command center may be used to better manage discharge needs. For example, one or more processors may determine that approximately 20% of patients from an acute-care hospital require medical transportation, such as in a wheelchair van or ambulance, to another treatment facility, such as a skilled nursing facility, acute rehab facility or post-acute rehab facility, or some other setting. Other exemplary patients may be at a venue for a medical appointment which may end at a particular time, after which they may require a ride home or to work. Healthcare command centers may monitor patient numbers and planned stay durations within a healthcare venue to scale transportation services to accommodate need over time. As a result, patients are transported quickly and do not have to wait after discharge for a transportation service to arrive to pick them up. Additionally, hospitals do not become backed up with discharged patients waiting for transportation to post-acute care venues, thus reducing numbers of extended stays. Healthcare command centers may monitor transportation needs throughout the day, week, and year to better anticipate future needs and to coordinate transportation services accordingly. Healthcare command centers may additionally monitor demand for particular type of transportation services overtime, as well as for time-sensitive discharges, such as patients who need to arrive at a secondary venue at a particular time. In this way, back-end EMS services are scalable to current and projected demand.

In some embodiments, a healthcare command center may include virtual reality systems and/or augmented reality systems integrated into the healthcare command center for simulations of the healthcare command center. These simulations may be utilized to support healthcare command center space design, workflow validation, and for training purposes. For example, an exemplary healthcare command center may provide a virtual reality simulation, for example through virtual reality (VR) goggles. The simulation may depict the spatial design of a healthcare command center, such as a planned future healthcare command center. The simulation may provide a number of templates pertaining to different features that a user may select to build a simulated healthcare command center. Templates may include, for example, transfer center resources, central bed placement resources, utilization review resources, admissions teams, financial services, and EMS and helicopter dispatch services. In the simulation, the user may lay out selected resources throughout the space to visualize how the space would look and operate. The user may additionally simulate planning over time for future needs or for future expansion of current resources. The simulation may enable the user to review a variety of factors such as the required furniture and materials, work flow, the layout of the different resources in the center, and interactions between different resources. This may enable simulated development of a team within the center. Alternatively or additionally, a plurality of users may view the same simulation, and may build a simulated healthcare command center together in the simulation.

In some embodiments, a healthcare command center may provide virtual-reality simulations and/or augmented-reality simulations to enable virtual engagement between geographically distant healthcare venues or individuals. For example, in a healthcare system with a number of hospitals which are geographically distant, users from each of those hospitals may enter into a virtual-reality simulation or an augmented-reality simulation integrated with the healthcare command center. For example, the simulation may be held in the place of a daily conference telephone call to discuss management of patient flow and the barriers to it. In the simulations, the users may view data together at the same time, and may view each other and may gesture to each other. The simulation may provide active engagement between users and may allow better sharing and analysis of data in the group setting. Alternatively or additionally, simulations may be held with multiple users to discuss complex patients who may have confounding issues. For example, a healthcare venue may admit an international patient with a set of complexities such as personal security details and embassy resources. Instead of calling or emailing sensitive data concerning this patient between users, the users may instead meet in a simulation. This may provide better sharing of information between users while allowing protection of that shared information.

In some embodiments, a healthcare command center may provide virtual-reality simulations and/or augmented-reality simulations to enable virtual healthcare command center extension to users in remote health venues. Examples of remote health venues may include ambulances and rural clinics. Users in remote health venues may benefit from periodic immersive healthcare command center team engagement. By providing these users with virtual-reality simulations, these remote users may engage users in the healthcare venue without having to travel to the venue. Additionally, simulation users may include staff and/or caregivers within a healthcare venue who do not have time to travel through the venue to a meeting room. These users may include case management workers. By holding a virtual-reality simulation instead of an in-person meeting, a case management worker may interact with other users in the simulation without having to waste time traveling to the meeting.

In some embodiments, a healthcare command center may provide virtual-reality simulations and/or augmented-reality simulations for training purposes. For example, newly hired healthcare command center staff may be trained in a virtual-reality simulation.

In some embodiments, a healthcare command center may provide virtual-reality simulations and/or augmented-reality simulations when the physical healthcare command center is inaccessible or otherwise unavailable, such as during a catastrophic failure such as a hurricane. In the event that staff cannot physically access the healthcare command center, they may hold a virtual-reality simulation instead from a safe location from which they may execute some or all of their regular duties.

In some embodiments, a healthcare command center may include agnostic call recording integration. For example, a healthcare command center may be integrated with one or more call recording services. Calls into the healthcare command center may be logged by the healthcare command center using various identifiers so that the calls may be accessed later and analyzed for trend detection and analysis. When a call is logged, a voice print from the call may be saved, as are various identifiers about the source of the call. The voice print and the associated data may be linked with one or more electronic records for later access and review. For example, when a patient places a 911 call, that call may enter the healthcare command center computer aided dispatch (CAD) system. The CAD may auto-populate the phone number, address, cross-street, local police department, first responders, and any other relevant information about the call source, and save the data with the unique identifier associated with that source. Alternatively, if the CAD receives a call from a source already associated with a unique identifier, the CAD may access that unique identifier and associated information, view historical data, and update the data if desired. In some embodiments, different call sources may each have a unique identifier with associated data and with which calls may be associated and stored. For example, individual patients and homes may have unique identifiers, as may other healthcare venues, systems, and healthcare command centers. As a result, when the healthcare command center receives a call from one of these sources, the dispatcher within the healthcare command center may view the information associated with the call to determine who is calling. The information may include historical data about the frequency of calls and the frequency of admissions. According to embodiments in which a call is received at the healthcare command center from a different healthcare venue, the call may include a unique identifier for the source of the call. The identifier may include, for example, the hospital from which the call is coming, as well as the floor number, room number, and optionally the individual placing the call. As a result, the staff member in the healthcare command center who receives the call may know the source of the call, may view data from past calls, and may log the current call into the history associated with the unique identifier. As a result, if resources are distributed as a result of the call, or if patients are transferred between healthcare venues as a result of the call, the healthcare command center may ensure that the resources and/or patients are sent to the correct venue.

Alternatively or additionally, in some embodiments, a call received at the healthcare command center may be assigned a unique patient identifier which may identify the patient or patients about whom the call concerns. As a result, the patient's record may include a history of calls relating to that patient, and the voice prints of those calls. This voice print data may be shared when the patient's record is shared between caregivers and/or between healthcare venues or systems.

In some embodiments, the patient's medical records, lab result data, transfer history, call history, and transaction case number may be associated using one or more electronic record links, for ease of access. In some embodiments, the aforementioned data may be associated with the patient's medical records, so that the medical records include historical lab result data, histories of calls about the patient, the patient's transfer history, and a history of patient's admissions across venues. This data may be maintained and updated over time.

In some embodiments, a healthcare command center may automatically generate and send end of shift reports. End of shift reports pertain to critical information collected during a given shift, such as high-level data. These reports may be sent to relevant staff and caregivers. In some existing healthcare systems, data is manually entered into the report by the shift supervisor. As a result, the report often has errors because of the manual entry, leading to an erosion of staff trust. In some embodiments, healthcare command center processors according to the present disclosure may track data during the shift in one or multiple databases, and may aggregate data from these databases to auto-generate the end of shift report. By automating generation and delivery of these reports, exemplary healthcare command centers provide crucial information to staff that is prompt and accurate. Alternatively or additionally, in some embodiments, the healthcare command center may be integrated with dashboards on a computer or personal device associated with staff and caregivers. Dashboards may provide staff and caregivers with continuous contextual information in real-time that is aggregated by and delivered from the healthcare command center. Staff and caregivers may personalize their individual dashboard to receive the most pertinent data.

In some embodiments, a healthcare command center may be integrated with an automated capacity operations status board. The board may be mounted within a healthcare venue and may provide visual indications of available capacities in specialty service units. These units may include trauma units, pediatrics, STEMI, stroke units, and neurosurgical units. Data depicted on the board may be collected, analyzed, and provided by the healthcare command center. The board may indicate the number of beds available in each unit, as well as available staff and resources. The board may indicate these available capacities visually, such as by depicting one or more of colors, numbers, letters, and symbols. For example, the board may utilize a color scheme indicating the availability in each unit, wherein a green indicator means the unit may receive additional patients with no or minimal delay in care, a yellow indicator means the unit may be capable of receiving additional patients but that resources may be limited and/or there may be a delay in care, and a red indicator means the unit may not accept any additional patients and/or may be short on resources and/or staff. The red indicator may suggest to other units and to other healthcare venues not to send additional patients to that unit, and to find a next available unit.

For example, if a unit which previously had open beds exceeds its ability to take on additional patients, the status of that unit may change in the board from green to red. A staff member or caregiver within the unit may change the indicator manually. Additionally or alternatively, processors within the healthcare command center may collect and analyze data for each unit and may execute algorithms to determine if the unit has exceeded its ability to take on additional patients. Healthcare command center processors may also execute algorithms to predict future trends in the ability of a unit to receive additional patients. If the healthcare command center determines that an indicator status change is necessary, it may automatically change the indicator without manual action by a staff member or caregiver. Alternatively, it may suggest the indicator status change to a staff member or caregiver.

According to some embodiments, the healthcare command center processors may analyze data to determine current demands on specialty service units, as well as the available capacities of each unit. Using machine learning and/or other artificial intelligence methods, the processors may generate projections of demands on each of the units and may offer suggestions to a user in response to these projections. For example, the healthcare command center may determine that a particular unit will shortly see an influx in patients due to a large traffic accident. The healthcare command center may analyze the current and projected demands of the trauma unit and may offer one or more options to the board user. For example, if the healthcare command center determines that the unit is not capable of handling additional patients after patients from the traffic accident are admitted, it may offer a first suggestion to change the indicator for that unit to red, and a second suggestion to change the indicator for that unit to yellow. The healthcare command center may prioritize one suggestion over the other. For example, the healthcare command center may suggest a red indicator as the best option and a yellow indicator as the second-best option. These prioritizations may be validated by a board user. The healthcare command center may track which suggestion the user selects in a given situation and may execute machine learning algorithms to optimize the prioritization of suggestions according to received data.

Alternatively or additionally, in some embodiments, a change in indicator status on the board may trigger automated responses from the healthcare command center and the systems controlled by the healthcare command center. For example, if a user changes the indicator for a unit to red, it may trigger mustering of additional resources and staff to send to that unit. The change in indicator may also cause the healthcare command system to generate alternative transportation plans for prospective patients. For example, if a patient plans to be transferred from a first unit to a second unit, in the case that the second unit's indicator changes to red, the healthcare command center may generate a plan to transport that patient to an alternative unit, either within the same healthcare venue or at a different healthcare venue.

In some embodiments, a healthcare command center may calculate wellness indices for all patients in a healthcare venue, and may record and track changes in indices over time. The healthcare command center may generate a baseline parameter for each patient and monitor their associated indices overtime, as compared to the baseline. In some embodiments, the healthcare command center may interface with one or more third party systems for providing collected data and receiving a calculated health index or clinical stability indicator for one or more patients. The healthcare command center may be associated with various devices throughout the healthcare venue, such as patient monitors, patient headboard devices, caregiver's personal devices, and desktop computers. Caregivers may use these devices to view the wellness indices for a given patient, as well as to view historical trend data and baseline data for that patient. Index data may be displayed in real-time. The wellness index may be used to assess the wellness of the patient. The historical data may be used to assess the patient's status overtime and whether the patient's health is improving or deteriorating.

In some embodiments, a healthcare command center may provide an on-call web based system which may perform direct messaging. Such a system may allow messaging without integration into an external phone system. The system may be connected with a scheduling program.

Figure 2:
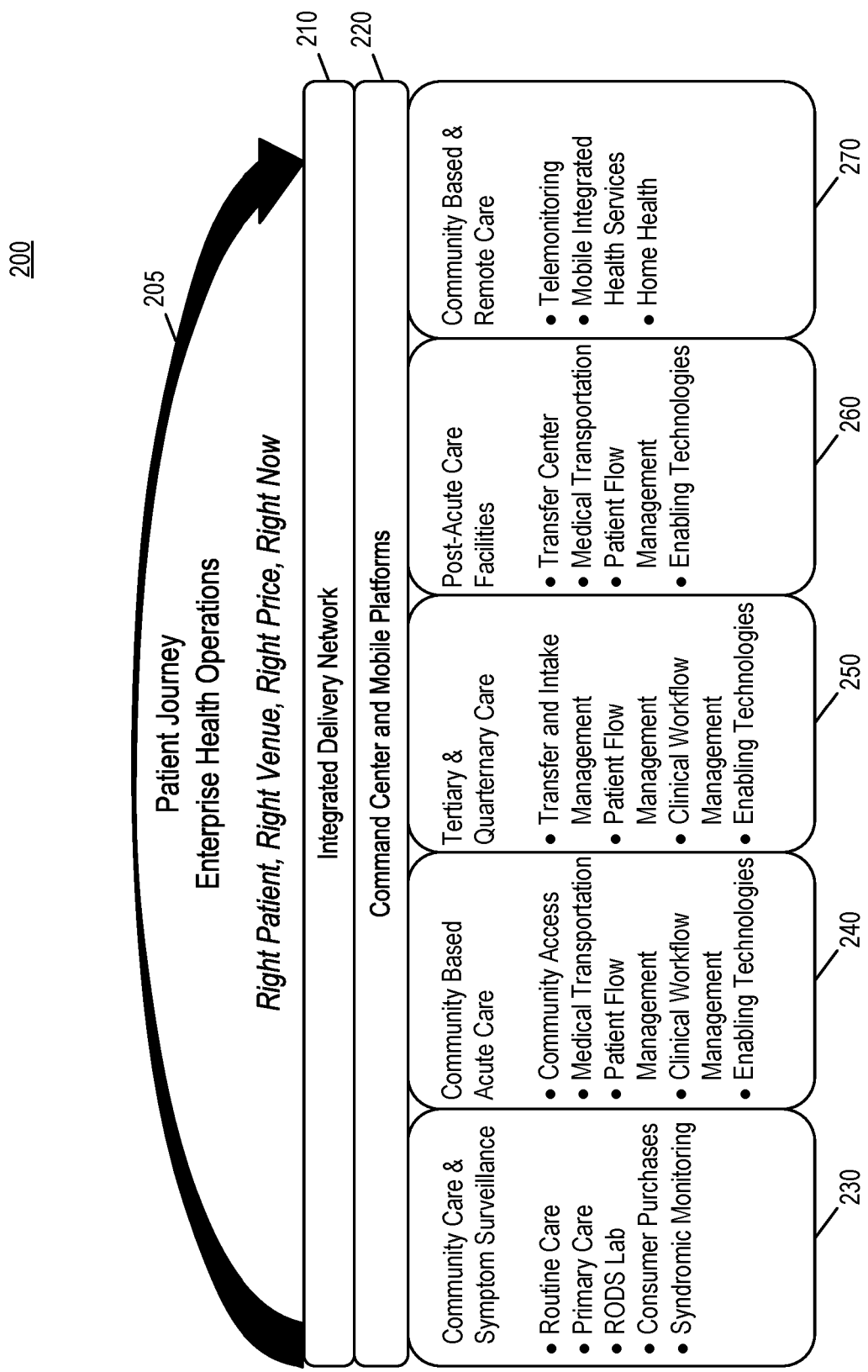
FIG. 2 depicts an exemplary diagram of example data channels in the context of a healthcare context, consistent with embodiments of the present disclosure.

FIG. 2 depicts an exemplary diagram of integrated health operations 200 which can be executed by system 100. Integrated health operations 200 may include integrated delivery network 210 and/or command center and mobile platforms 220. In some embodiments, a user interface may be displayed on one or more devices within a command center, such as terminal 140 (e.g., an example command center), to enable a user to view and/or perform operations of FIG. 2. Additionally or alternatively, such a user interface may be available in a global format, such as for display on mobile device 120 (e.g., an example mobile platform). In various embodiments, system 100 can access various data streams to aggregate patient and community information, and utilize the collected data to intelligently control the care delivery network. In some embodiments, the data streams may include community care and symptom surveillance 230, community-based acute care 240, tertiary and quaternary care 250, post-acute care facilities 260, and/or community-based and remote care 270. For example, collected data may be utilized to anticipate the needs of a community and to manage the flow of patients, caregivers, supplies and facilities accordingly. As shown by arrow 205, exemplary system 100 may coordinate these resources to meet anticipated needs, such as a spreading illness within the community, while minimizing costs associated with wasted time and resources. For example, system 100 may contact a healthcare provider to initiate a perimeter vaccination of an area, request shipment of consumable supplies, medicines, and vaccines to an area, adjust staffing and intake procedures at a healthcare facility and/or generate an advisory for the area.

In various embodiments, exemplary system 100 may collect information about a given patient and their medical history, and may utilize the information to route the patient to the best venue of care. For example, a patient experiencing a chronic back injury may call 911 because he is experiencing pain. In such circumstances, it may be unnecessary for the patient to come into the emergency department, given the high cost of emergency care and because a more appropriate care venue is available. System 100 may access the patient's medical history and analyze factors such as the patient's plan of care, appointment history, medications, and his physical location, and may use these factors to determine the best treatment option. For example, system 100 may determine that the patient has recently missed a physiotherapy appointment and has not filled his recent prescription for pain medication. System 100 may schedule an appointment for the patient at a physiotherapy clinic, such as a clinic where the patient was previously treated. Optionally, system 100 may coordinate with a transportation service, such as taxi service, or a ride-share service such as Lyft®, or Uber®, to transport the patient to the clinic at the appropriate time. For example, system 100 may use an application programming interface (API) of a ride-sharing service to request transportation from an individual's location to a healthcare facility. Additionally or alternatively, system 100 may determine that the patient may be best treated using telemedicine techniques, which may be performed by utilizing output from sensors 185. For example, the patient may speak to a practitioner over the phone or by video chat, or can receive messages (e.g. emails or text messages) generated and sent by the system 100 to prescribe a specific treatment plan. System 100 may transmit a text message with a link to a patient, which when selected, may initiate a video conference with a telemedicine professional. Alternatively or additionally, system 100 may transmit the contact information to a database of a telemedicine provider, and the telemedicine provider may initiate contact with the patient. Advantageously, the patient may receive the most appropriate care for his condition, and time and resources may be saved because the patient did not need to visit the emergency department and/or did not unnecessarily utilize emergency transportation services.

In various embodiments, system 100 may collect symptom indicator information from resources throughout the community. For example, system 100 may access consumer purchase information, such as from a Real-Time Outbreak and Disease Surveillance (RODS) Lab barcode scanning and points of sale tracking system. In some embodiments, system 100 may access this information via third party server 170. Such information may indicate when citizens in the community are making purchases due to a developing health condition. Additionally or alternatively, system 100 may access syndromic monitoring systems and RODS Lab data, such as real-time outbreak and disease surveillance data, and may use the data to determine and track health phenomena within the community. For example, system 100 may receive anonymized digital health records from healthcare providers, which may include information such as symptoms and diagnoses (e.g., step, meningitis, a positive tuberculosis test, an HIV positive test, communicable diseases, drug usage, drug addiction, narcotics usage). System 100 may aggregate this healthcare provider data from different hospitals in a given area to identify issues unique to a given location. System 100 may incorporate additional information in this determination, such as data about the weather, pollen, and time of year and season, which may be provided by sensor 185 and correlated with a given location. For example, system 100 may determine an increase in flu medicine purchases, and may use that data to predict a number of patients likely to present to facilities 102 with flu symptoms, and when they are likely to do so. In another example, system 100 may determine that purchases of cold and allergy medicine are indicative of seasonal allergies, due to a detected high pollen count and the current season. In another example, system 100 may determine a food borne illness in certain zip codes based upon purchases of anti-diarrheas and the anti-nausea medications in those zip codes.

System 100 may develop and execute community interventions as a result of a determined health phenomenon. For example, in the event that food borne illness is detected in certain zip codes, system 100 may develop and output public safety announcements through media, and/or may alert caregivers and hospital employees to refrain from engaging in certain illness-causing activities. As another example, system 100 may deploy an early vaccination program, such as in hospitals, schools, and churches, when it detects an earlier-than-usual spread of influenza. For example, system 100 may access a database of patients, query the database to identify patients with an age exceeding a predetermined threshold (e.g., more than 75 years old), and transmit an electronic request to schedule an appointment for a vaccination (e.g., send an email or text message with a link to a scheduling platform for a healthcare provider). For patients who are less mobile or immobile, system 100 may schedule a mobile treatment provider to travel to a patient's location and administer a vaccine at the patient's residence. By utilizing collected information to develop and execute community based and remote care, system 100 may proactively address health conditions within a community, often addressing the condition in its early stages.

In some embodiments, system 100 may monitor emergency and non-emergency transportation. For example, system 100 may monitor transportation of patients to an emergency department, both by EMT services and by non-emergency services such as taxi, Lyft, and Uber. In some embodiments, system 100 may retrieve patient admission data from local networks 110. Additionally or alternatively, system 100 may monitor patient admission in an Emergency Department Information System (EDIS) to monitor admission rates over time. System 100 may utilize this data to track trends in admissions, such as variability in admission numbers or the reasons for admission. System 100 may utilize this data to predict future patient numbers. For example, system 100 may determine an increase in admissions for influenza symptoms. In some embodiments, system 100 may correlate this analysis with an analysis of consumer purchases of flu medicine, as explained above. System 100 may determine an outbreak of influenza within a community and may use the data to predict the numbers of patients likely to present to the hospital, and when they are most likely to arrive. Using this data, system 100 may control orders of supplies for treating influenza, such as medicine, electrolyte beverages, and disposable supplies. While system 100 may maintain a baseline of supplies, it may determine that additional supplies are required due to an anticipated influx of patients, and may coordinate orders for extra resources in the supply chain. System 100 may use the anticipated number of patients to determine the number of resources needed, thus preventing over-ordering of materials which would go to waste.

Similarly, system 100 may utilize predictions of health phenomena in the community to control staffing schedules within a hospital. For example, if system 100 determines an outbreak of a contagion within the community that is likely to affect 20%-30% of the population, this contagion is likely to affect a requisite number of caregivers and staff employed by facilities 102. So just at the same time that demand for care increases from a patient care standpoint, available staffing numbers may decrease. System 100 may utilize a number of techniques to mitigate this effect. For example, it may increase the number of scheduled shifts, in anticipation that some staff members will ultimately miss scheduled shifts due to illness. It may also send alerts to caregivers and staff to notify them of the developing contagion and to suggest measures to avoid infection.

In some embodiments, exemplary system 100 may minimize a number of no-show appointments. For example, system 100 may identify a certain number of patients in a care system that are not showing up to their appointments. It may analyze the patient information to identify why the patients are missing their appointments. It may identify a lack of public transportation, and may coordinate with a transportation organization, such as Uber or Lyft, to get patients to their wellness check.

In some embodiments, exemplary system 100 may be configured for remote video care. Patients may be remotely located outside of a care facility, such as in their homes. These locations may be fitted within high definition cameras and microphones such that the system may monitor the patient's condition, such as sensors 185. Advantageously, the patient need not be transported to a facility 102 and can instead stay within their support environment with family and friends. While health outcomes for these remote care techniques are similar to in-patient care, they allow lower costs because there are no transportation costs and in-patient facilities 102 need not be utilized for these patients.

Additionally, exemplary system 100 may improve access of the appropriate patients to tertiary and quaternary care centers because non-critical patients may be treated using telemedicine techniques. The patients may remain in their homes, and system 100 may formulate a care plan for that patient based upon the remote monitoring and analysis of the patient's information. System 100 may remotely monitor the patient via sensors 185 to ensure that they are progressing according to their care plan, and that they are communicating with their care providers. If system 100 determines lack of progression, they may alert the care giver to contact the patient.

Figure 3:
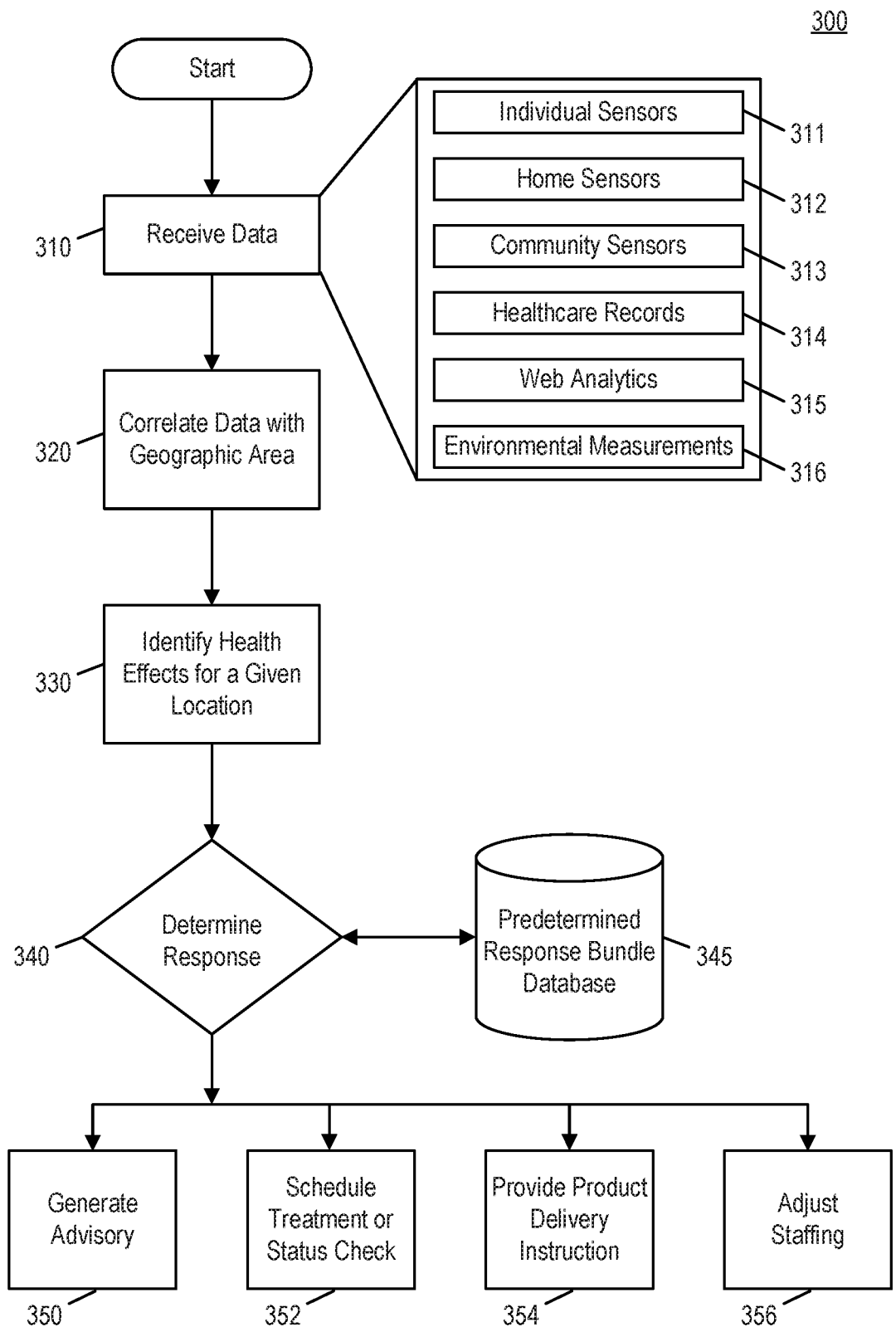
FIG. 3 depicts an exemplary flow diagram of transmitting digital data over a plurality of channels, consistent with embodiments of the present disclosure.

FIG. 3 depicts an exemplary flow diagram of process 300 for transmitting digital data over a plurality of channels, consistent with embodiments of the present disclosure. While certain components are discussed in relation to process 300, those components are intended to be merely exemplary. Additional and/or alternative components may also perform functions consistent with disclosed embodiments.

In step 310, process 300 may receive data from one or more sensors. System 100 may receive data through one or more public and/or private networks. For example, sensors may transmit encoded data over an internet protocol (IP) network to system 100. In other examples, sensors may transmit data to a third party, which may be accessed by system 100 through an application programming interface (API), database queries, and/or data scraping from one or more websites.

In some embodiments, step 310 may receive data from one or more example data sources. For example, process 300 may receive data from individual sensors 311, home sensors 312, community sensors 313, healthcare sensors 314, web analytics 315, and/or environment measurements 316.

Individual sensors 311 may include sensors worn or used by a single person. For example, individual sensors 311 may include a smartphone, smartwatch, heart rate monitor, blood glucose monitor, blood pressure monitor, and the like. Home sensors 312 may include sensors fixed within a single household. For example, home sensors 312 may include Internet-of-Things (IoT) devices, such as "smart" appliances, internet-connected thermostats, home security system sensors, cameras, proximity sensors, door sensors, smart pill bottles, and the like. Community sensors 313 may be sensors that receive data covering multiple households. For example, community sensors 313 may include shared bathroom sensors (e.g., soap dispenser sensors, water usage sensors), convenience store sensor sensors (e.g., universal product code (UPC) scanners, foot traffic detectors), and/or street sensors (e.g., traffic sensors, traffic cameras). Healthcare sensors 314 may be sensors that receive data from one or more healthcare facilities. For example, healthcare sensors 314 may provide data from electronic health records, patient flow, staffing measurements, patient test results and diagnoses, and other data entered, sensed, and/or stored within a healthcare provider's facility. Web analytics 315 may be data regarding internet traffic and search queries.

Environmental measurements 316 may be measurements about the environment, such as temperature, pressure, humidity, wind, UV-index, pollen count, and other meteorological measurements. Environmental measurements 316 may be received from third party weather services, such as the National Weather Service, or directly measurement using one or more networked meteorological sensors.

In step 320, process 300 may correlate data with one or more geographic areas. As data is received from one or more sensors, system 100 may assign it a geographic region. For example, in the case of weather, system 100 may indicate the geographic region associated with that temperature. For other types of data, it may indicate a pinpoint location (e.g., global positioning system (GPS) coordinates) as opposed to a region. For example, sales data for a store may be associated with the store's address. As another example, IoT appliance data for a given household may be labeled with the address of that house.

Each type of sensor data may form a separate "layer" on a geographic map, enabling system 100 to identify certain regions where specific combinations of factors occur. For example, it may determine that a certain region has been particularly cold, has high public transport traffic, and also above-average cough medicine sales, which may prompt system 100 to publish an advisory about how to prevent communicable diseases on public transportation.

In step 330, process 300 may identify health effects for a given location. In some embodiments, system 100 may derive user actions from sensors and correlate those actions and perceived symptoms to determine potential diagnoses. Referring back to the bathroom sensor example previously discussed, in addition to receiving sensor data about bathroom usage (e.g., from toilet water usage sensors and proximity sensors) as well as hand washing sensors (e.g., from sink water usage sensors and soap dispenser sensors), system 100 may also receive data from UPC scanners at pharmacies and convenience stores in the same geographic area. The UPC data may indicate that users are buying medication to treat a fever in addition to gastro-intestinal distress. Based on this example data, system 100 may derive potential systems, such as fever and gastro-intestinal distress (e.g., from the purchase drugs) as well as frequent bathroom usage (e.g., from the bathroom sensors). In this example context, system 100 may further receive data from healthcare facilities of reported symptoms and confirmed diagnoses. System 100 may determine whether the reported symptoms match the perceived symptoms and, when they match, identify the confirmed diagnoses as possible diagnoses for the symptoms of the area. In this way, system 100 may be able to more quickly identify an outbreak of a viral infection, such as the norovirus.

In step 340, process 300 may determine a response (if any) for a given health effect (e.g., a health affect determined in step 330). System 100 may match the determined medical effect with predetermined actions. In the context of the norovirus example, system 100 may determine that a public advisory should be issued. However, in other examples, where the health effect may be a something that can be treated by a vaccine, a perimeter vaccination program may be initiated for the area.

In some embodiments, step 340 may include consulting database 345. System 100 may query the database with one or more potential diagnoses to determine action that system 100 can take in response. The database may return certain actions, such as actions correlated with a confidence value associated with the diagnosis. System 100 may determine a confidence level for each diagnosis (e.g., the likelihood that the potential diagnosis is correct) and then perform the actions that have corresponding confidence levels associated with them. The use of the confidence levels may avoid taking certain actions that may be more costly or intensive when the likelihood of usefulness is lower.

In some embodiments, system 100 may determine a classification associated with the potential diagnoses and query database 345 with the classification. Example classifications may include minor outbreak, viral epidemic, ongoing problem, and the like. In another example, a numerical level corresponding to the severity of the potential diagnoses may be used.

Process 300 may perform one or more actions, such as in response to determining an appropriate action (e.g., as determined in step 340). These actions may include, for example, step 350, step 352, step 354, and/or step 356. In step 350, process 300 may generate an advisory. For example, system 100 may generate a message to advise community members and/or individuals of a health issue that may affect them and/or preventative steps they can take. As an example, system 100 may publish a post on social media, alert local media (e.g., create a draft press release), and/or initiate a television, internet, and/or radio ad with the advisory.

In step 352, process 300 may schedule a treatment for a patient or schedule a healthcare provider to contact a patient. System 100 may transmit a request to a health providers portal for an appointment for an at-risk community member and also transmit a message to the patient notifying them of the recommended appoint (e.g., via email, recorded phone message, and/or text message). Alternatively or additionally, system 100 may transmit a request to a healthcare provider (e.g., nursing staff of a primary care physician) to reach out to a patient who may be affected.

In step 354, process 300 may generate product delivery instructions. System 100 may transmit instructions to send consumable resources from areas of surplus to areas of need. Depending on the diagnosis, system 100 may submit a request to ship healthcare supplies (e.g., syringes, bandages) and medicine (e.g., vaccines, prescription drugs, over-the-counter drugs) from one healthcare provider that is outside an area affected by a health effect to a healthcare provider in the area. In the context of initiating a perimeter vaccination, system 100 may submit a request to a hospital to ship vaccine supplies to proximate healthcare facilities.

In step 356, process 300 may adjust staffing at a healthcare provider. Similar to meeting the demand for certain supplies, system 100 may also meet staffing demands. For example, in the example of setting up a perimeter vaccination, system 100 may also evaluate staffing (e.g., using a health provider's human resources portal) to ensure adequate staff are available to administer vaccinations. In still other examples, system 100 may call in on-call physicians to assist with associated medical needs. In the example context of system 100 generating a list of at-risk patients to contact, system 100 may ensure that there are enough staff on hand to reach out to at-risk patients. For example, system 100 may determine the number of patients to be reached, multiply that by the expected call length, and determine how many hours it would be likely to take to make all the calls. If needed, system 100 may contact off-duty staff to see if they can assist with additional calls.

Command centers consistent with disclosed embodiments may be implemented as part of a system for multi-channel communication that interfaces electronic devices associated with patients, family members, transporters, caregivers, personal physicians, as well as third party systems. A detailed scenario is described below to illustrate an example of implementing a command center in such a system.

A first electronic device (such as user device 120) may be associated with a caregiver, such as an obstetrician-gynecologist "Katie." Katie's electronic device may automatically receive a schedule of cases for the day from a command center, implemented in this example by facility server 130. Katie's electronic device may receive the schedule upon entering a local network of the facility (such as a hospital), and generate a graphical user interface displaying the cases. Meanwhile, 16-year old Maggie drives off to school on her own for the first time.

Meanwhile, in a private doctor's office outside the hospital, Samantha, who is eight months pregnant, is being examined by another caregiver user Elizabeth, in a doctor's office. During the examination, an electronic device such as Elizabeth's tablet computer may automatically transcribe physician notes based on detected voice input from Elizabeth. Samantha exhibits sudden distress characterized by abnormally high blood pressure and swelling. Elizabeth's tablet computer (an example of public member device 194) may generate and transmit a request for an emergency transport from the doctor's office to the hospital. The request may be generated automatically based on detected sensor readings, or may be generated based on a voice or tactile input from Elizabeth to the tablet. The tablet may transmit the request to the Command Center (facility server 130) via network 150. Computer terminal 140 at the hospital may receive the request, and generate a graphical user interface displaying the request information. At the same time, facility server 130 may automatically initiate a search for nearby and available transport vehicles, while a specialist "Betty" observes the displayed request information.

Facility server 130 may receive an indication from Betty identifying Katie as the on-call obstetrician-gynecologist (OBGYN) at the hospital, or facility server 130 may automatically identify Katie as the on-call OBGYN based on stored scheduling data. The system may initiate a three-way call between Katie, Elizabeth, and Betty to discuss Samantha's condition. Facility server 130 may propagate information for generating graphical user interfaces showing real-time details of Samantha's case to electronic devices associated with each of Katie, Elizabeth, and Betty during the three-way call, and facility server 130 may automatically transcribe the call into a case file generated for Samantha. Facility server may receive an indication of a bed request from computer terminal 140 operated by Betty, and the system may determine and display a list of tests that must be ordered or scheduled based on the case notes stored for Samantha. At the same time, facility server 130 may cause computer terminal 140 to indicate to Betty that a transport vehicle has been automatically dispatched for Samantha. Facility server 130 may also transmit information to electronic devices for Katie and Elizabeth to display the updated case status and an estimated time of arrival of the transport vehicle with Samantha at the hospital.

Meanwhile, in an emergency transport vehicle, an emergency medical technician driver Frank is finishing dropping off a patient, and an electronic device associated with Frank, such as Frank's smartphone or a device installed in the transport vehicle, receives the transport request generated and sent from facility server 130 for Samantha. Frank's device application detects an input indicative of accepting the request, and the electronic device application automatically retrieves and provides a graphical user interface showing directions to Samantha's current location. While en route, Frank passes a recent four-car accident on the highway, and asks his electronic device detects a voice-activated command and input with information about the four-vehicle accident, which is processed and transmitted to facility server 130 of the command center. Facility server 130 may generate and provide an alert to computer terminal 140 associated with specialist Betty, and may provide an option to automatically initiate a voice call with Frank's electronic device to gather more details. Depending on the received data and additional details from Frank, facility server 130 or Betty may search for and locate additional optional two Emergency Medical Services (EMS) vehicles, and reroute a selected EMS vehicle to the scene of the reported accident. Facility server 130 may also generate and provide an alert notification to the Emergency Department of the facility of the pending arrival of multiple patients for later that day, from the accident. Thus, in some embodiments, an electronic device running an application that interfaces with facility server 130 may receive an emergency transport request from facility server 130, and search for the nearest available transportation option, such as EMS vehicles in close geographical proximity to the patient(s), and having current or expected availability. Once the transportation option is secured, the application may generate and provide directions to the location of the emergency.

In some embodiments, an electronic device application may receive a report with information about potential patients, such as individuals involved in a new accident that are expected to be transported to the facility. In such embodiments, the electronic device application may receive an emergency transport request, and initiate a search for the nearest available transportation option. Once secured, the transportation option will be routed to the scene. The application may also generate and provide an alert to the Emergency Department of the facility about incoming patients that are en route to the hospital via the secured emergency transport.

Meanwhile, at the hospital facility, an anesthesiologist Mike is finishing up a surgery, and his electronic device receives information about a potential emergency C-section (for Samantha) that is automatically added to his schedule for later that day. Mike's electronic device may generate a graphical user interface providing details about patient Samantha, and Samantha's diagnosis.

At the same time, supervisor Betty may receive a call from the police on scene about the traffic accident, and may be informed that five crash victims are severely injured. Facility server 130 may transcribe the call and detect information for generating new case files that are automatically populated with details provided by the automatically transcribed call. Facility server 130 and/or Betty may initiate a search to locate more Emergency Medical Services trucks, and may automatically route them to the crash site. Facility sever 130 may also automatically update the Emergency Department electronic records, and provide a prompt on Betty's electronic device to schedule five bed requests. Throughout this exemplary scenario, facility server 130 may generate and provide one or more notifications and graphical user interfaces to operations executive Ron, to notify him of the surge in patients due to the traffic accident, the actions and protocols that are automatically implemented, as well as the expected outcomes upon completion of the initiated protocols.

In another doctor's office external to the hospital facility, patient Jacob is being examined by his allergist Deborah who administers two allergy shots to his arms. Deborah's electronic device may detect a voice activation command and voice input including a detected instruction to set a reminder for checking on Jacob in thirty minutes. The electronic device may generate a visual or audible output confirming the set reminder. Thus, in some embodiments, an electronic device application can receive a request for a reminder from a healthcare practitioner, and a voice-activated system may generate and output a confirmation the request and remind the practitioner according to the set reminder.

Responsive to the electronic device reminder, Deborah returns to check on Jacob. She may notice that he is struggling to breathe, and Deborah may quickly administer a dose of epinephrine. Deborah's electronic device may detect a voice or tactile command input for requesting an emergency transport for Jacob. Deborah's electronic device may automatically collect data about Jacob's condition from one or more connected sensor devices and recent medical record entries, and automatically transmit the data with the emergency request. Facility server 130 may receive the emergency transport request and medical condition data, and generate one or more graphical user interfaces for providing on computer terminal 140 associated with Betty. Facility server 130 may automatically locates an Emergency Medical Services truck proximate to Deborah's office where Jacob is located, and may automatically route the truck with receipt of an input indicating Betty's confirmation. Facility server 130 may continuously collect real-time data, and propagate automatic updates to electronic devices associated with Betty (at the hospital), Deborah (in her doctor's office), and the Emergency Department (at the hospital) with the expected arrival time and additional clinical/logistical details.

The EMS trucks transporting both Samantha and Jacob arrive in the Emergency Department, and both patients are stabilized. Emergency Department caregivers prepare Samantha for an emergency C-section. Facility server 130 may update one or more electronic records and generate one or more electronic notifications indicating that Samantha and Jacob are within the facility, and provide their care status.

Yet another potential patient, Erica, is leaving her house with her husband whose hand is uncontrollably bleeding due to a recent accident. The two are headed to the Emergency Room. An electronic device associated with Erica may initiate a search using a patient application for recommended Emergency Rooms, based on the geographic location of Erica's electronic device, and real-time expected wait times for the nearby Emergency Rooms as indicated by one or more facility servers or a Command Center facility server. Erica's electronic device may select the Emergency Room having the shortest wait time and within a reasonable distance, either automatically or based on input from Erica, and the electronic device may automatically generate and provide directions to the Emergency room. During the trip, the electronic device may provide questions requesting input, resulting in Erica and her husband being automatically checked in to the Emergency Room. The electronic device may continuously generate and provide update to Erica and her husband during their trip about the wait time of the selected Emergency Room. The electronic device may detect received input, such as an indication on an electronic pain scale from Erica, who notices that the pain in her husband's hand becoming worse, The Emergency Department electronic device may receive one or more electronic notifications with Erica and her husband's expected arrival time as well as details about her husband's case such as the detected pain scale inputs.

Thus, in some embodiments, the electronic device application may provide suggested emergency rooms proximate to the electronic device and having real-time wait time information, and may receive and transmit medical information to a selected Emergency Room electronic device while the patient is en route to the Emergency Room, and even if the patient is traveling without the assistance of medical professionals.

Erica's electronic device may generate and provide an alert that the selected Emergency Department wait time is now significantly longer than previously reported, and may request input regarding whether to reroute to another Emergency Department with a shorter wait time. The electronic device may detect in input to reroute, and may automatically adjust and the directions and route to the new Emergency Department notified. Erica's electronic device may also request an input regarding whether Erica would like to inform her family of the Emergency Department. Upon detecting an affirmative input. the electronic device may cause the generation and propagation of instant electronic notifications to pre-approved and previously-registered family member electronic device, with updated Emergency Department details, including directions and expected arrival times to the new Emergency Department based on the geographical locations of the family member device(s).

Thus, in some embodiments, the electronic device application may automatically update emergency room wait times and offer an opportunity to prospective patients in commute to a particular emergency room to reroute to an alternative emergency room with a shorter wait time. The electronic device application may additionally automatically check patients into a particular emergency room while in route.

At the Emergency Department (ED), an electronic device associated with ED triage nurse Nora may detect a voice input from Nora asking about the current wait time while examining a patient. Facility server 130 may provide the requested wait time information to Nora's electronic device, and the electronic device may generate and output an indication of the wait time. Upon detecting a significant increase in wait time, Facility server 130 may propagate an update message to Nora's electronic device, prompting another visual or audible output to inform Nora of the increased wait time due to the detection of multiple new patients that are being transported to the Emergency Department. Due to the increased wait time, Nora's electronic device may automatically query Nora for input regarding whether she would like additional help at the Emergency Department.

Thus, in some embodiments, the electronic device applications may generate and output updates regarding patient wait times, and alert healthcare personnel of wait time adjustments that may require increases in staffing, to automatically adjust staffing based on statistical analysis of wait times and patient transport levels.

Following a detection of Nora's request for additional help, Nora's electronic device (or facility server 130) may generate and transmit a request for three additional nurses to head to the Emergency Department. Facility server 130 may generate and provide a graphical user interface to Betty, with the request and a graphical representation of the nurses that facility server 130 has determined have the most availability in their predetermined schedule and based on their current real-time assigned tasks. An electronic device associated with Marcus, a unit charge nurse, may receive an alert indicating that three of his nurses are needed in the Emergency Department. Marcus' electronic device may provide a graphical user interface for receiving selection of one or more preselected messages, which when selected, may be transmitted to one or more nurse electronic devices with details about the arriving patients. Facility server 130 may receive an indication of the reassigned nurses, and one or more notifications about the three nurses' updated patient assignments may be automatically reported.

Thus, in some embodiments, an electronic device application may receive a request for staff for a department that is determined by the facility server 130 to ne understaffed based on current and expected patient volumes and current and expected wait times. Facility server 130 may identify potential additional nurses by searching for nurses with the most availability in their schedule and current task assignment lists, automatically assign available nurses to particular patients or particular departments, and generate and send one or more electronic notifications to electronic devices associated with nurses, to display information about their respective patient assignments, and, if necessary depending on availability, reassign healthcare personnel.

Meanwhile, Nora's electronic device may provide information regarding the five crash victims while they are in transit from the accident site via Emergency Medical transport. After consulting with the emergency medical technicians, Nora may conclude that all five victims will require intensive care unit beds and one victim, Maggie, will require surgery. Upon receiving information input from Nora, facility server 130 may generate and send one or more electronic notifications to an electronic device associated with Karl, a hospital transport aide. Based on the received electronic notifications, Karl is notified to transport Maggie to the operating room upon arriving to the hospital. Computer terminal 140 associated with Betty may receive electronic notifications indicating the arrival of the five crash victims and their change in status in one or more records updated by facility server 130. Facility server 130 may also generate one or more bed requests, either automatically or based on input from Betty, which are sent to one or more electronic devices associated with the intensive care unit and associated staff.

An electronic device associated with anesthesiologist Mike may receive an electronic alert of another add-on case associated with Maggie's surgery. Mike's electronic device may provide electronic record data associated with the case, and Maggie's expected arrival time based on the geographic location and traffic status of the Emergency Medical Services transport, so he can effectively prepare. Facility server 130 may automatically add electronic devices of Mike and Karl to a communication channel for the care team associated with Maggie's case. Facility server 130 may propagate messages with Maggie's status and estimated time of arrival to electronic devices associated with each of the surgical staff, the larger care team, and pre-registered devices associated with Maggie's family members. Each electronic device may receive the information relevant to the associated person.

Facility server 130 may detect a potential bottleneck in the post-anesthesia care unit unless four patients are discharged within a predetermined time period, and facility server 130 may generate and send a warning message to computer terminal 140 associated with Betty. Another electronic device associated with Darla, a post-anesthesia care unit charge nurse, may receive and display the alert about the potential bottleneck, in particular that two emergent cases from the Operating Room are at risk of being blocked from entry. Facility server 130 may receive an input from Darla identifying two patients that can be discharged, or facility server 130 may automatically identify patients that have begun the discharge process or are close to discharge, and facility server 130 may initiates the entry and discharge processes for the respective patients. Facility server 130 may automatically generate and transmit electronic notifications to electronic devices associated with the care teams and family members of the patients to be discharged. Thus, in some embodiments, electronic device applications may generate warnings about potential bottleneck in departments of the hospital based on historical and trending data patterns, and may provide suggestions for relocating or discharging patients to avoid the patient bottleneck, also automatically providing updates to electronic devices associated with family members of the patients and relevant personnel of the patients' respective care teams about the patients' relocations.

Prior to discharge, one of the two patients may be automatically assigned to a rehab specialist and tele-health physician for recurring appointments at the patient's home, by facility server 130 updating an electronic record associating the patient with the rehab specialist and tele-health physician, and scheduling one or more appointments based on patient and specialist/physician schedule information. Facility server 130 may generate and transmit an electronic notification to an electronic device associated with hospital transport aide Karl, to move a patient from the post-anesthesia care unit to a hospital floor. Electronic devices associated with the patient's care team may be automatically updated with Karl's assignment, and his expected arrival time. As previously mentioned, facility server 130 may continuously monitor hospital operation statuses and provide updates to an electronic device associated with operations executive Ron, to inform him that all actions and protocols have been completed with positive outcomes.

Meanwhile, a personal electronic device associated with Samantha's husband Robert may receive a notification that Samantha is being transported to the Emergency Department. The electronic device application may request input from Robert to indicate whether he would like transportation to the hospital. Upon receiving input from Robert, facility server 130 may dispatch a hospital carshare service to the location of Robert's electronic device. Robert's electronic device may receive and provide real-time details of Samantha's condition while being transported to the hospital. As Robert's electronic device approaches the hospital, it may receive and display an indication of Samantha's location within the hospital. In some embodiments, the carshare may be included with the hospital service, and therefore Robert may exits the car without having to worry about payment. Upon request, Robert's electronic device application may provide navigation information to Samantha's current location in the hospital. Electronic devices associated with Samantha's care team may also receive updates on Robert's electronic device location while commuting to and within the hospital. Thus, in some embodiments, electronic devices applications can be used by pre-approved family members to request a form of transportation, such as a car share service, to the hospital. The electronic device application may simultaneously update electronic devices for a responsible care team about the status of both the patient and as well as any pre-approved family members intending to visit the hospital.

Robert's electronic device may be pre-programmed to generate an audible or visual notification of any updates from facility server 130 or electronic devices associated with Samantha's care team. Thus, Robert's electronic device application may inform him of the expected finish time for Samantha's surgery, so he can head back to the waiting room. In the waiting room, an on-call obstetrician-gynecologist Katie is waiting to relay news to Robert that Samantha's surgery was successful and the couple has a new baby. At the same time, facility server 130 may automatically generate and transmit one or more notifications across multiple communication channels to electronic devices associated with Samantha's family members and care team, and to computer terminal 140 associated with the command center specialist Betty.

Returning to the accident victims, a personal electronic device associated with Maggie's may receive a message from an electronic device associated with the on-call surgeon, reassuring Maggie's father that Maggie will be fine.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may include a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects of the invention.

Embodiments may be implemented with computer-executable instructions. The computer-executable instructions may be organized into one or more computer executable components or modules. Embodiments may be implemented with any number and organization of such components or modules. For example, aspects of the disclosure are not limited to the specific computer-executable instructions or the specific components or modules illustrated in the figures and described herein. Other embodiments may include different computer-executable instructions or components having more or less functionality than illustrated and described herein.

When introducing elements of aspects of the disclosure or the embodiments thereof, the articles "a," "an," and "the" are intended to mean that there are one or more of the elements. The terms "comprising," "including," and "having" are intended to be inclusive and mean that there may be additional elements other than the listed elements.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer-readable media, or existing communications software.

What is claimed is:
1. A computing system, comprising:
at least one processor;
a storage medium storing instructions that, when executed, configure the at least one processor to perform operations comprising:
receiving, at a healthcare command system associated with a medical facility, data from a plurality of sources through one or more networks, wherein at least a subset of the plurality of sources is external to the medical facility;
assigning each of the data from the plurality of sources to one of a plurality of geographic regions by identifying a geographic location associated with each of the data and assigning data having a geographic location within a defined geographic region to the corresponding geographic region;
determining health effects for a predetermined location within a target one of the plurality of geographic regions based on the data assigned to the target geographic region, wherein the determining comprises predicting a clustered health condition within the target geographic region from the data assigned to the target geographic region;
generating, by querying a predetermined response database, instructions in view of the determined health effects for the predetermined location, the instructions including an action and an associated device, wherein the generating occurs at least partially before patients affected by the clustered health condition present at the medical facility; and transmitting, to the associated device, the action associated with the instructions.

2. The computing system of claim 1, wherein the plurality of sources includes one or more of: individual sensors, home sensors, community sensors, healthcare records, web analytics, and environmental measurements.

3. The computing system of claim 1, wherein the action includes one or more of:
   instructions for generating an advisory via a social media application programming interface,
   instructions for scheduling a treatment with an electronic scheduling platform of a healthcare provider,
   instructions for causing an electronic order to ship a product to a healthcare provider, and
   instructions for an electronic staffing database for a healthcare provider.

4. The computing system of claim 1, wherein:
   the data includes sales of one or more over-the-counter drugs, and
   the plurality of sources includes a universal product code scanner.

5. The computing system of claim 4, wherein determining health effects comprises:
   comparing the sales of the one or more over-the-counter drugs to a database of historical sales data to identify whether the sales exceed a predetermined threshold;
   querying, when the sales exceed the predetermined threshold, one or more pharmaceutical databases to determine symptoms treated by the one or more over-the-counter drugs; and
   querying one or more diagnosis databases to determine potential diagnoses based on the determined symptoms.

6. The computing system of claim 5, wherein generating the instructions comprises:
   responsive to determining that a vaccine exists for one of the potential diagnoses, transmitting instructions to a healthcare provider in the target geographic region to initiate a perimeter vaccination of the target geographic region that administers a vaccine.

7. The computing system of claim 6, wherein generating the instructions further comprises:
   transmitting a request to a healthcare provider outside the target geographic region to ship a supply of the vaccine to the healthcare provider in the target geographic region.

8. A method for receiving and transmitting digital data over a plurality of channels comprising:
   receiving, at a healthcare command system associated with a medical facility, data from a plurality of sources through one or more networks, wherein at least a subset of the plurality of sources is external to the medical facility;
   assigning each of the data from the plurality of sources to one of a plurality of geographic regions by identifying a geographic location associated with each of the data and assigning data having a geographic location within a defined geographic region to the corresponding geographic region;
   determining health effects for a predetermined location within a target one of the plurality of geographic regions based on the data assigned to the target geographic region, wherein the determining comprises predicting a clustered health condition within the target geographic region from the data assigned to the target geographic region;
   generating, by querying a predetermined response database, instructions in view of the determined health effects for the predetermined location, the instructions including an action and an associated device, wherein the generating occurs at least partially before patients affected by the clustered health condition present at the medical facility; and
   transmitting, to the associated device, the action associated with the instructions.

9. The method of claim 8, wherein the plurality of sources includes one or more of: individual sensors, home sensors, community sensors, healthcare records, web analytics, and environmental measurements.

10. The method of claim 8, wherein the action includes one or more of:
    instructions for generating an advisory via a social media application programming interface,
    instructions for scheduling a treatment with an electronic scheduling platform of a healthcare provider,
    instructions for causing an electronic order to ship a product to a healthcare provider, and
    instructions for an electronic staffing database for a healthcare provider.

11. The method of claim 8, wherein:
    the data includes sales of one or more over-the-counter drugs, and
    the plurality of sources includes a universal product code scanner.

12. The method of claim 11, wherein determining health effects comprises:
    comparing the sales of the one or more over-the-counter drugs to a database of historical sales data to identify whether the sales exceed a predetermined threshold;
    querying, when the sales exceed the predetermined threshold, one or more pharmaceutical databases to determine symptoms treated by the one or more over-the-counter drugs; and
    querying one or more diagnosis databases to determine potential diagnoses based on the determined symptoms.

13. The method of claim 12, wherein generating the instructions comprises:
    responsive to determining that a vaccine exists for one of the potential diagnoses, transmitting instructions to a healthcare provider in the target geographic region to initiate a perimeter vaccination of the target geographic region that administers a vaccine.

14. The method of claim 12, wherein generating the instructions further comprises:
    transmitting a request to a healthcare provider outside the target geographic region to ship a supply of the vaccine to the healthcare provider in the target geographic region.

15. A non-transitory computer-readable medium storing instructions that, when executed by one or more processors, cause the one or more processors to perform a method for receiving and transmitting digital data over a plurality of channels comprising:
    receiving, at a healthcare command system associated with a medical facility, data from a plurality of sources through one or more networks, wherein at least a subset of the plurality of sources is external to the medical facility;
    assigning each of the data from the plurality of sources to one of a plurality of geographic regions by identifying a geographic location associated with each of the data and assigning data having a geographic location within a defined geographic region to the corresponding geographic region;

determining health effects for a predetermined location within a target one of the plurality of geographic regions based on the data assigned to the target geographic region, wherein the determining comprises predicting a clustered health condition within the target geographic region from the data assigned to the target geographic region;

generating, by querying a predetermined response database, instructions in view of the determined health effects for the predetermined location, the instructions including an action and an associated device, wherein the generating occurs at least partially before patients affected by the clustered health condition present at the medical facility; and transmitting, to the associated device, the action associated with the instructions.

16. The medium of claim 15, wherein the plurality of sources includes one or more of: individual sensors, home sensors, community sensors, healthcare records, web analytics, and environmental measurements.

17. The medium of claim 15, wherein the action includes one or more of:
   instructions for generating an advisory via a social media application programming interface,
   instructions for scheduling a treatment with an electronic scheduling platform of a healthcare provider,
   instructions for causing an electronic order to ship a product to a healthcare provider, and
   instructions for an electronic staffing database for a healthcare provider.

18. The medium of claim 15, wherein:
   the data includes sales of one or more over-the-counter drugs, and
   the plurality of sources includes a universal product code scanner.

19. The medium of claim 18, wherein determining health effects comprises:
   comparing the sales of the one or more over-the-counter drugs to a database of historical sales data to identify whether the sales exceed a predetermined threshold;
   querying, when the sales exceed the predetermined threshold, one or more pharmaceutical databases to determine symptoms treated by the one or more over-the-counter drugs; and
   querying one or more diagnosis databases to determine potential diagnoses based on the determined symptoms.

20. The medium of claim 19, wherein generating the instructions comprises:
   responsive to determining that a vaccine exists for one of the potential diagnoses, transmitting instructions to a healthcare provider in the target geographic region to initiate a perimeter vaccination of the target geographic region that administers a vaccine.

* * * * *